(12) United States Patent
Lin et al.

(10) Patent No.: US 9,074,886 B2
(45) Date of Patent: Jul. 7, 2015

(54) LINE-WIDTH MEASUREMENT DEVICE AND MEASUREMENT METHOD USING THE SAME

(75) Inventors: Yung-yu Lin, Guangdong (CN); Qingping Wang, Guangdong (CN)

(73) Assignee: SHENZHEN CHINA STAR OPTOELECTRONICS TECHNOLOGY CO., LTD., Guangdong (CN)

( * ) Notice: Subject to any disclaimer, the term of this patent is extended or adjusted under 35 U.S.C. 154(b) by 382 days.

(21) Appl. No.: 13/700,400

(22) PCT Filed: Jul. 19, 2012

(86) PCT No.: PCT/CN2012/078887
§ 371 (c)(1),
(2), (4) Date: Nov. 27, 2012

(87) PCT Pub. No.: WO2014/008679
PCT Pub. Date: Jan. 16, 2014

(65) Prior Publication Data
US 2014/0009602 A1   Jan. 9, 2014

(51) Int. Cl.
*H04N 7/18* (2006.01)
*G01C 11/02* (2006.01)
*G01B 11/02* (2006.01)
(Continued)

(52) U.S. Cl.
CPC .............. *G01C 11/025* (2013.01); *G01B 11/02* (2013.01); *G01B 2210/56* (2013.01); *G01N 21/95684* (2013.01)

(58) Field of Classification Search
CPC .... G01B 11/02; G01B 11/022; G01B 11/024; H04N 7/18; H04N 7/181; H04N 17/00; H04N 17/004; H04N 17/04; H04N 17/02; H04N 17/002; H04N 17/045; H04N 9/093; G06T 7/0018; G06T 7/408; G06T 7/0081
USPC ......... 348/135–137, 142, 180, 182, 188, 187; 382/108, 109, 165
IPC ................................. H04N 7/18, 17/00, 17/02
See application file for complete search history.

(56) References Cited

U.S. PATENT DOCUMENTS 8,436,890 B2   5/2013  Mamiya
2009/0316959 A1*  12/2009  Shibata et al. ................ 382/108
(Continued)

FOREIGN PATENT DOCUMENTS

CN   1576831   2/2005
CN   101311706   11/2008
(Continued)

*Primary Examiner* — Sherrie Hsia
(74) *Attorney, Agent, or Firm* — Kirton McConkie; Evan R. Witt

(57) ABSTRACT

A line-width measurement device and a measurement method using the same are disclosed. The line-width measurement device has a platform, an image capturing device and a color-mixing light source device. The image capturing device captures an image of a pattern under measurement in a measurement area of the platform. The color-mixing light source device correspondingly provides illumination to the measurement area. The color-mixing light source device has a plurality of monochromatic light sources and adjusts the brightness scale of each monochromatic light source according to the matching rate of the pattern under measurement and a standard pattern to provide suitable color-mixed lights for illumination. Therefore, the present invention can provide a better measurement environment to further enhance accuracy of line-width measurement.

13 Claims, 5 Drawing Sheets

(51) Int. Cl.
*G01N 21/956* (2006.01)

(56) References Cited

U.S. PATENT DOCUMENTS

2010/0289893 A1* 11/2010 Yoo et al. .................. 348/135
2012/0113246 A1    5/2012 He et al.

FOREIGN PATENT DOCUMENTS

| CN | 101761874  | 6/2010  |
|----|------------|---------|
| CN | 101889190  | 11/2010 |
| CN | 102095377  | 6/2011  |
| JP | 1313745    | 12/1989 |
| JP | 2001249084 | 9/2001  |

* cited by examiner

LINE-WIDTH MEASUREMENT DEVICE AND MEASUREMENT METHOD USING THE SAME

BACKGROUND OF THE INVENTION

1. Field of the Invention

The present invention relates to a line-with measurement technology, especially to a line-width measurement device and a measurement method using the same that increase accuracy of line-width measurement.

2. Description of the Related Art

With the development of semiconductor manufacturing process, integrated circuit elements are progressively made much smaller. Therefore, in the semiconductor manufacturing process, control of critical dimension, such as line width, line pitch, etc. of fine circuit patterns on masks or wafers, is an important point. Generally, manufacturers use line-width measurement device to measure critical dimensions of circuit patterns, the line-width measurement device can be used to inspect if the line width or pitch is precise without deviation.

With reference to FIG. 1, FIG. 1 is a schematic view of performing line-width measurement according to a conventional technology. The conventional technology uses an image capturing device 91 (such as a CCD camera) to capture an image from a pattern 92 under measurement, and then performs line-width measurement through computer processing. The image capturing device is usually assembled together with a light source device 90. The light source device 90 provides illumination in a forward direction on a top of the pattern 92 under measurement, so that the image capturing device is able to capture a clear image.

The captured image is colored and will be converted into a gray scale image for the operation of line-width measurement. In general, before a computer performs line-width measurement of the gray scale image, it will first load an image of a standard pattern as a measuring reference. With reference to FIG. 2, lights from the light source device 90 in FIG. 1 will pass through a filter 93 to provide suitable illumination so that the gray scale image converted from the captured image can have similar color contrast with the standard pattern for performing line-width measurement. The filter 93 used in the light source device for line-width measurement generally includes five kinds of filter units 930 having different colors to provide different choices of colored illumination so that different gray scale images can be obtained by using the lights projected through the different filter units 930.

However, when the gray scale image of the pattern under measurement has a big difference in color contrast with the standard pattern, it will affect the accuracy of line-width measurement. Because foregoing filter 93 only provides five kinds of filter units 930, the light source device 90 can only provide five kinds of colored illumination. Since different patterns under measurement may be made of materials having different reflection characteristics, only five choices of colored illumination will have limited room to adjust the gray scale image of the pattern under measurement.

Therefore, it is necessary to provide a line-width measurement device and a measurement method using the same to overcome the problems existing in the conventional technology.

SUMMARY OF THE INVENTION

In view of the shortcomings of the conventional technology, the main objective of the invention is to provide a line-width measurement device and a measurement method using the same that provide more illumination choices of colored light source, so as to solve the technical problem in which the gray scale image of the pattern under measurement has a difference in color contrast with the standard pattern and thereby affecting the accuracy of line-width measurement.

In order to achieve the foregoing object of the present invention, the present invention provides a line-width measurement device comprising:

a platform having a measurement area;

an image capturing device mounted above the platform and used to capture an image of a pattern under measurement in the measurement area;

a color-mixing light source device mounted above the platform, including a plurality of monochromatic light sources and adjusting brightness scale of each of the monochromatic light sources according to a matching rate between the image of the pattern under measurement and an image of a standard pattern.

In one embodiment of the present invention, the line-width measurement device further comprises a controller, and the controller is connected to the image capturing device and receives the image of the pattern under measurement captured by the image capturing device.

In one embodiment of the present invention, the controller is further connected to the color-mixing light source device and is used to control the color-mixing light source device to adjust the brightness scale of each of the monochromatic light sources according to the matching rate between the image of the pattern under measurement and the image of the standard pattern.

In one embodiment of the present invention, the controller is further used to convert the image of the pattern under measurement to a gray scale image, and then compare the gray scale image with the image of the standard pattern so as to confirm the matching rate between the gray scale image and the image of the standard pattern.

In one embodiment of the present invention, when the matching rate is larger than or equal to 80%, the controller is further used to measure widths of lines in the gray scale image; when the matching rate is lower than 80%, the controller then controls the color-mixing light source device to adjust the brightness scale of each of the monochromatic light sources.

In one embodiment of the present invention, the color-mixing light source device has a red light source, a blue light source and a green light source which provide 256 kinds of colored illumination by color mixing.

In one embodiment of the present invention, the red light source, the red light source, the blue light source and the green light source are at least one red light-emitting diode, at least one blue light-emitting diode and at least one green light-emitting diode, respectively.

The present invention further provides a line-width measurement method comprising steps of:

S101: loading a standard pattern;

S102: using a color-mixing light source device having a plurality of monochromatic light sources to provide illumination to a measurement area;

S103: scanning the measurement area to capture an image of a pattern under measurement;

S104: converting the image of the pattern under measurement to a gray scale image and then comparing the gray scale image with the image of the standard pattern so as to confirm the matching rate between the gray scale image and the image of the standard pattern; and S105: when the matching rate is larger than or equal to a specific value, measuring widths of lines in the gray scale image; or when the matching rate is lower than the specific value, adjusting the brightness scale of each of the monochromatic light sources and providing illumination again and re-executing steps S103, S104 and S105.

In one embodiment of the present invention, the specific value is 80%.

In one embodiment of the present invention, the color-mixing light source device has a red light source, a blue light source and a green light source; and adjusting the brightness scale of each of the monochromatic light sources in step S105 is to adjust the brightness scale of the red light source, the blue light source and the green light source.

The present invention further provides another line-width measurement device comprising:

a platform having a measurement area;

an image capturing device mounted above the platform and being used to capture an image of a pattern under measurement in the measurement area;

a controller connected to the image capturing device and receiving the image of the pattern under measurement captured by the image capturing device; and a color-mixing light source device mounted above the platform, including a plurality of monochromatic light sources and adjusting brightness scale of each of the monochromatic light sources according to the matching rate between the image of the pattern under measurement and an image of a standard pattern so as to provide suitable color-mixed lights for illumination, wherein the color-mixing light source device includes a red light source, a blue light source and a green light source.

In one embodiment of the present invention, the color-mixing light source device further has an optical element; and the lights emitted by the monochromatic light sources are together projected onto the optical element and mixed with each other, and then are projected outwardly after passing through the optical element.

The present invention uses the color-mixing light source device to correspondingly provide illumination to the measurement area. The color-mixing light source device includes a plurality of monochromatic light sources and is able to adjust the brightness scale of each monochromatic light source according to the matching rate of the image of the pattern under measurement and the image of a standard pattern so that it can provide suitable mixed colored lights for illumination and further reduce the difference in color contrast between the gray scale image of the pattern under measurement and the image of the standard pattern, effectively increase the accuracy of line-width measurement.

DETAILED DESCRIPTION OF THE PREFERRED EMBODIMENTS

The foregoing objects, features and advantages adopted by the present invention can be best understood by referring to the following detailed description of the preferred embodiments and the accompanying drawings. Furthermore, the directional terms described in the present invention, such as upper, lower, front, rear, left, right, inner, outer, side and etc., are only directions referring to the accompanying drawings, so that the used directional terms are used to describe and understand the present invention, but the present invention is not limited thereto.

Figure 1:
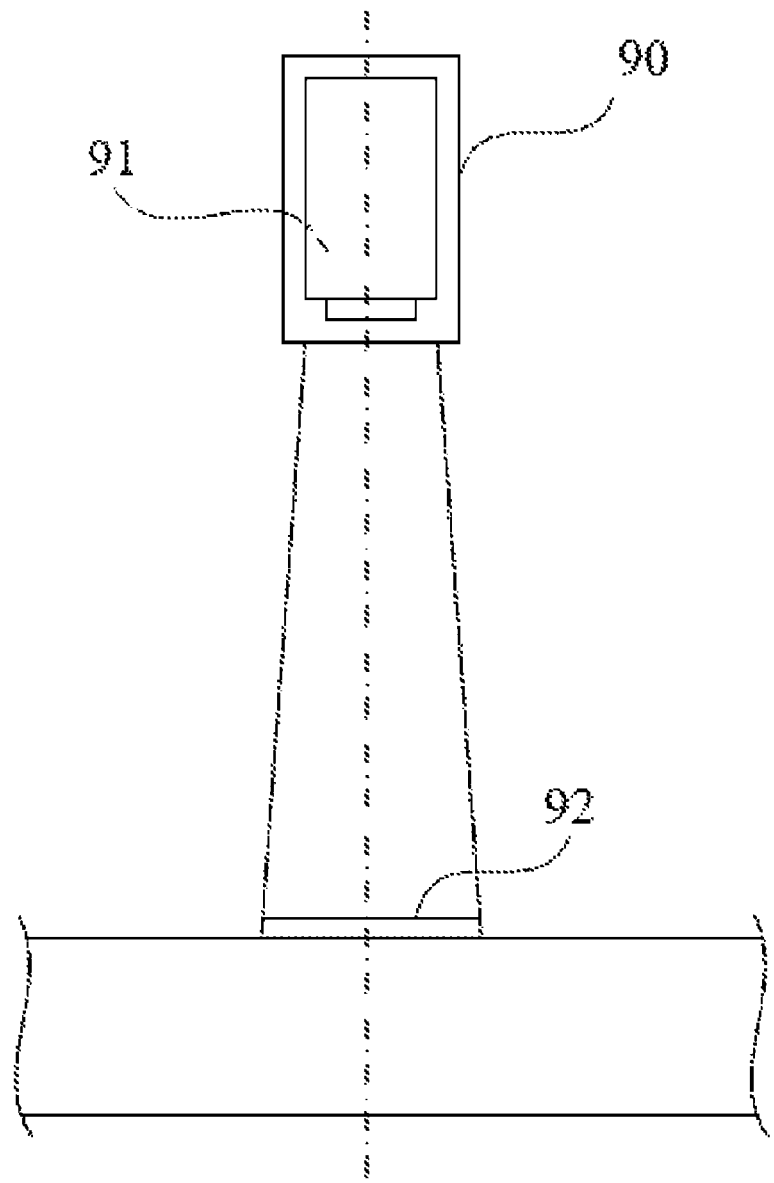
FIG. 1 is an operational view of a conventional line-width measurement device.
Figure 2:
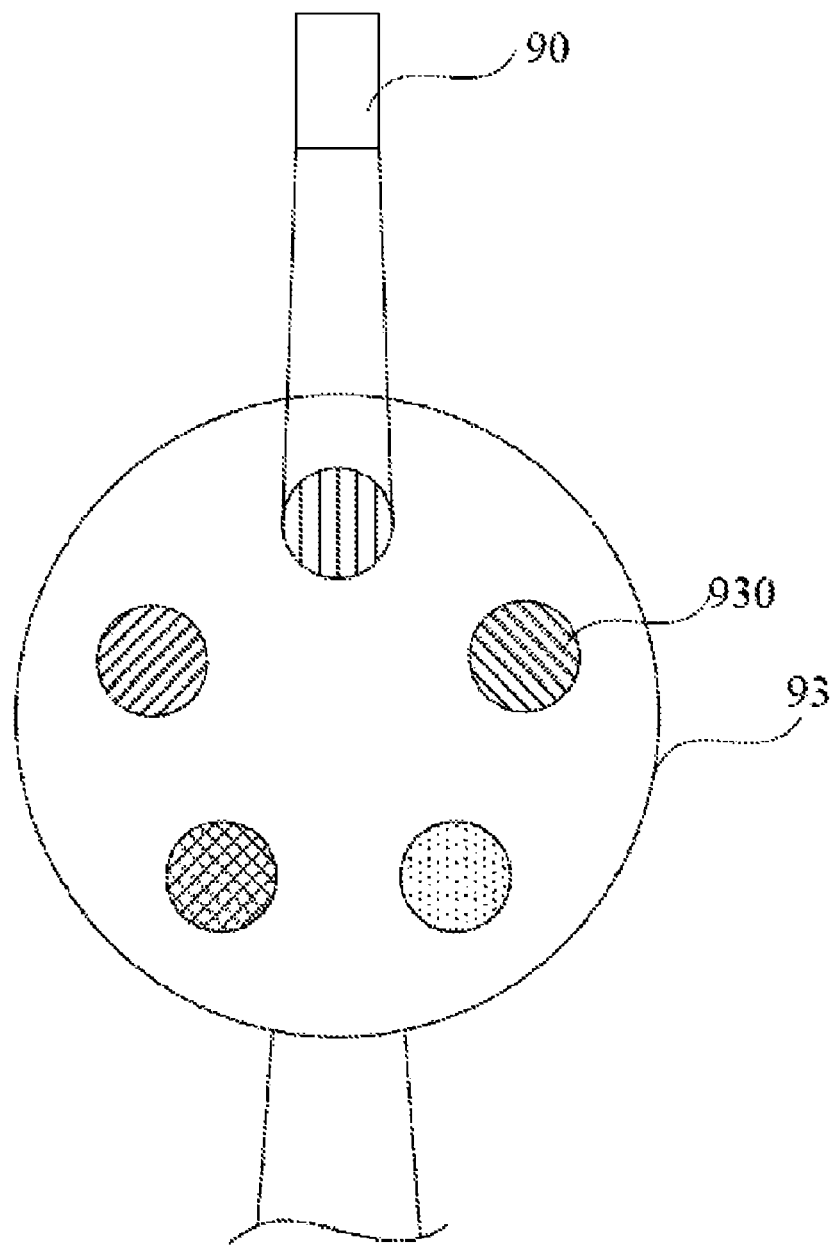
FIG. 2 is an operational view showing that a light source device projecting lights through a filter of the conventional line-width measurement device.
Figure 3:
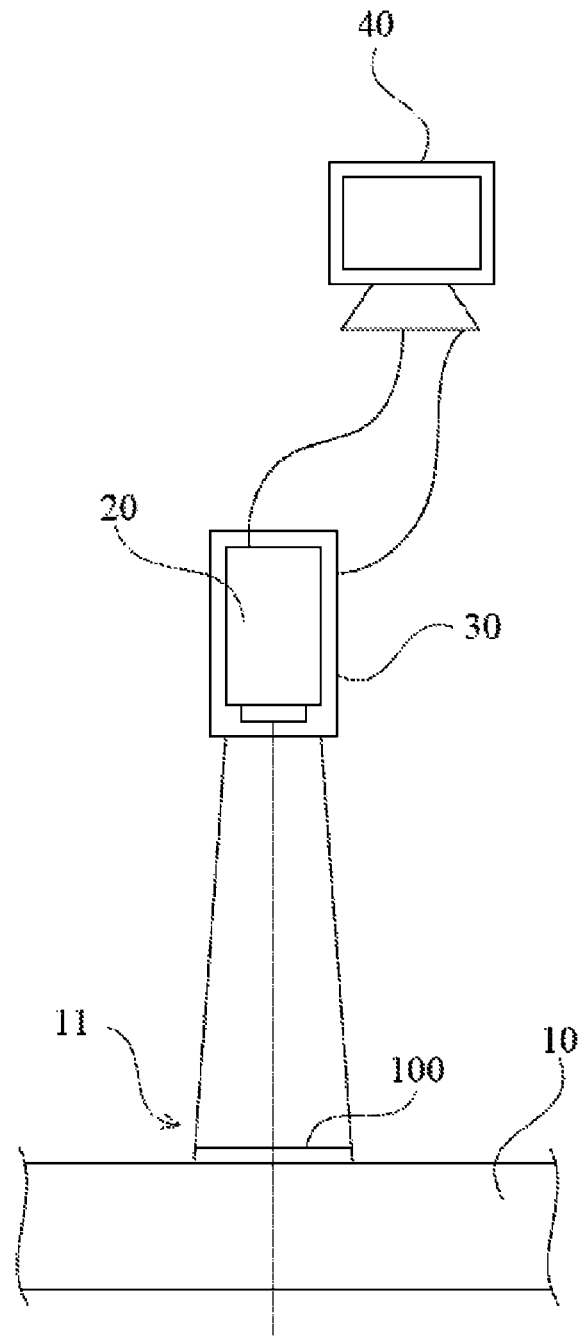
FIG. 3 is an operation view of a preferred embodiment of a line-width measurement device in accordance with the present invention.

With reference FIG. 3, FIG. 3 is an operation view of a preferred embodiment of a line-width measurement device in accordance with the present invention. The line-width measurement device comprises a platform 10, an image capturing device 20 and a color-mixing light source device 30.

The platform 10 has a measurement area 11. The measurement area 11 is positioned on a top surface of the platform 10 for placing a pattern 100 under measurement (i.e. to be measured). The pattern under measurement 100 mainly refers to related components in the field of liquid crystal display device, such as an indium tin oxide (ITO) transparent electrode of a liquid crystal panel, data lines, scanning lines, etc., but is not limited thereto.

The image capturing device 20 is mounted above the platform 10 and may be attached to a bracket (not illustrated in the figures) mounted on the platform 10. The image capturing device 20 preferably is aligned with and faces the measurement area 11 of the platform 10 and captures an image of the pattern 100 under measurement in the measurement area 11.

Figure 4:
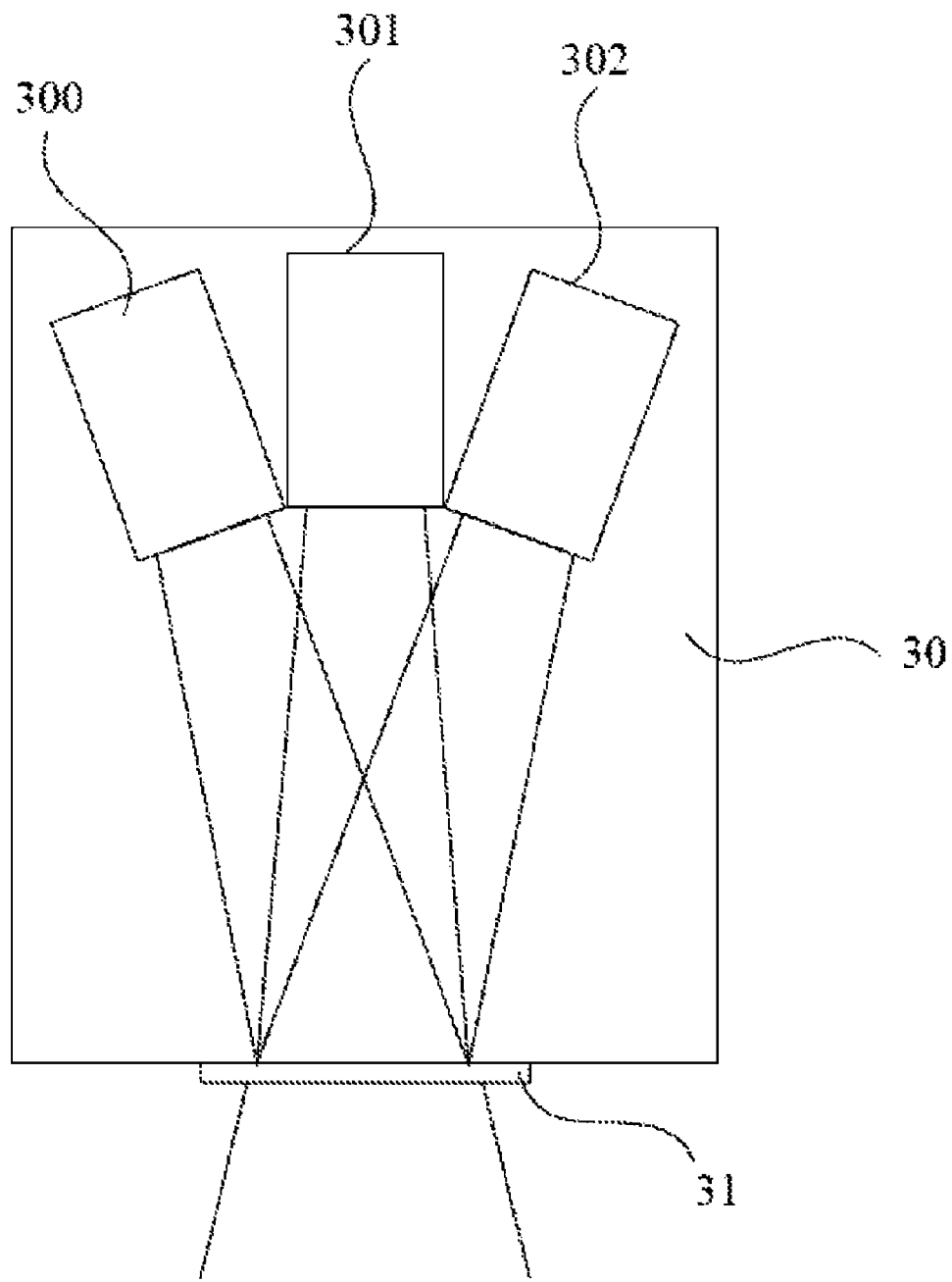
FIG. 4 is a schematic view of a preferred embodiment of a color-mixing light source device of the line-width measurement device in accordance with the present invention.

The color-mixing light source device 30 is mounted above the platform 10. The color-mixing light source device 30 correspondingly provides forward illumination to the measurement area 11, and an incident direction of the forward illumination is perpendicular to the surface of the platform 10. The color-mixing light source device 30 may be a light-emitting diode (LED) assembly. With further reference to FIG. 4, FIG. 4 is a schematic view of a preferred embodiment of the color-mixing light source device 30 of the line-width measurement device in accordance with the present invention. The color-mixing light source device 30 includes a plurality of monochromatic light sources. In this embodiment, the monochromatic light sources include a red light source 300, a blue light source 301 and a green light source 302. The red light source 300, the blue light source 301 and the green light source 302 preferably are at least one red light-emitting diode, at least one blue light-emitting diode and at least one green light-emitting diode, respectively. The color-mixing light source device 30 can adjust brightness scale of each of the monochromatic light sources according to the matching rate between the image of the pattern 100 under measurement and an image of a standard pattern so as to provide suitable color-mixed lights for illumination. When the monochromatic light sources are the red light source 300, the blue light source 301 and the green light source 302, the color-mixing light source device 30 can provide 256 kinds of colored illumination by color mixing. Furthermore, the color-mixing light source device 30 may further have an optical element 31, such as a lens; and the lights emitted by the monochromatic light sources may be projected onto the optical element 31 together and be mixed with each other, and then be projected outwardly after passing through the optical element 31.

The line-width measurement device may further comprises a controller 40. The controller 40 is connected to the image capturing device 20 and is used to receive the image of the pattern under measurement captured by the image capturing device 20. In this embodiment, the controller 40 is further connected to the color-mixing light source device 30 and is used to control the color-mixing light source device 30 to adjust the brightness scale of each of the monochromatic light sources according to the matching rate between the image of the pattern 100 under measurement and the image of the standard pattern. The controller 40 is further used to convert the image of the pattern 100 under measurement to a gray scale image, and then compare the gray scale image with the image of the standard pattern so as to confirm the matching rate between the gray scale image and the image of the standard pattern. When the matching rate is larger than or equal to a specific value, the controller 40 then further measures widths of lines in the gray scale image; or when the matching rate is lower than the specific value, the controller 40 then further controls the color-mixing light source device 30 to adjust the brightness scale of each of the monochromatic light sources. In this embodiment, the specific value is preferably 80%, wherein the matching rate refers to the degree of similarity in color contrast between the gray scale image and the image of the standard pattern.

Since the color-mixing light source device 30 is used to provide illumination, the color-mixing light source device correspondingly adjust the brightness scale of each of the monochromatic light sources according to the matching rate between the pattern under measurement and the standard pattern, and thereby providing suitable colored illumination by mixing colored lights. Suitable colored illumination allows the gray scale image of the pattern under measurement to have similar color contrast with the standard pattern. In this way, the controller 40 can measure the widths of the lines in the pattern 100 under measurement more accurately.

Figure 5:
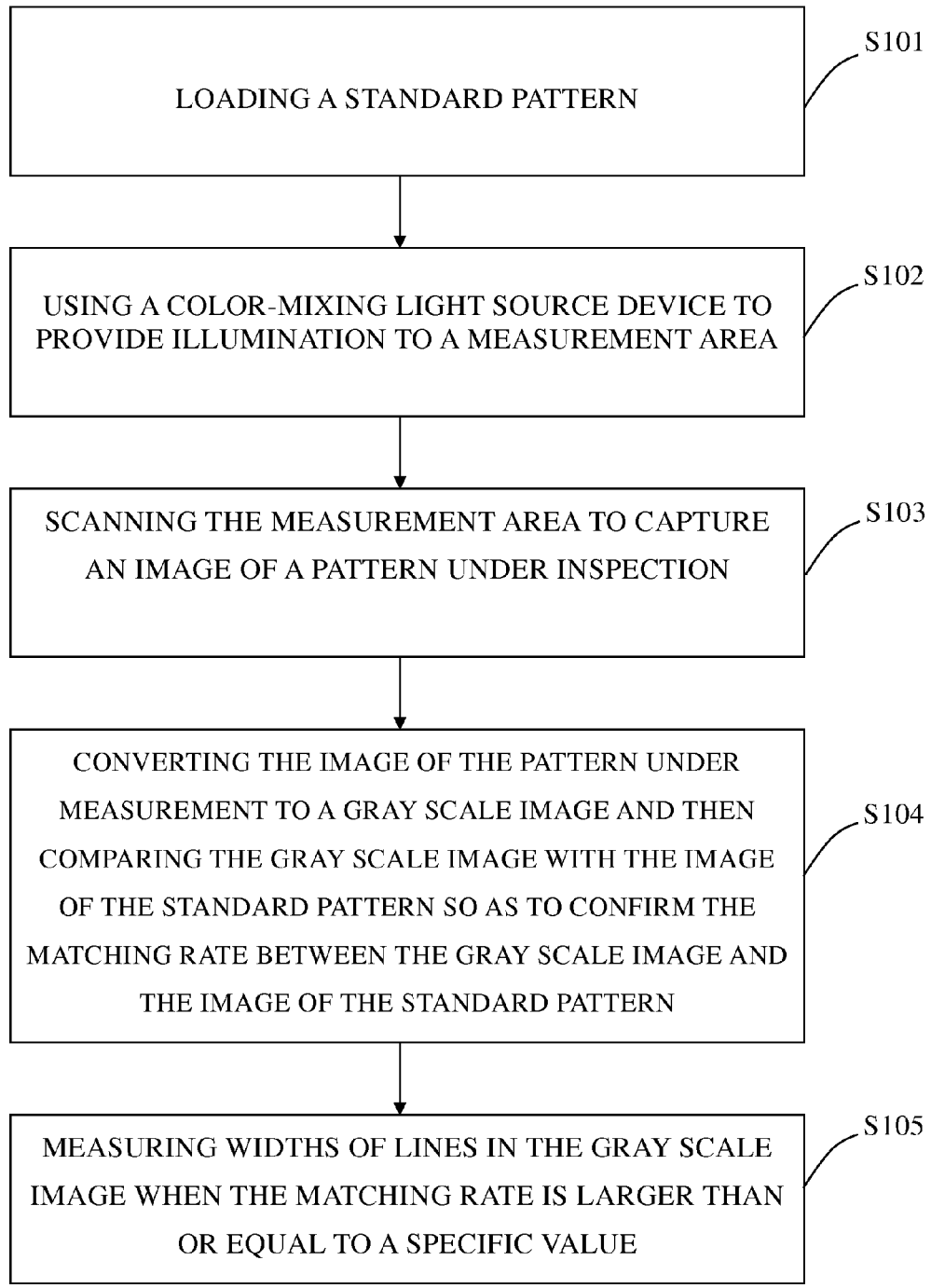
FIG. 5 is a flow chart of a preferred embodiment of a line-width measurement method in accordance with the present invention.

The line-width measurement device may be operated by a line-width measurement method. The line-width measurement method, with reference to FIG. 5, comprises steps of:

S101: loading a standard pattern;

S102: using a color-mixing light source device to provide illumination to a measurement area 11;

S103: scanning the measurement area 11 to capture an image of a pattern 100 under measurement;

S104: converting the image of the pattern 100 under measurement to a gray scale image and then comparing the gray scale image with the image of the standard pattern so as to confirm the matching rate between the gray scale image and the image of the standard pattern; and S105: when the matching rate is larger than or equal to a specific value, then further measuring widths of lines in the gray scale image.

Besides, in step S105, when the matching rate is lower than the specific value, then further adjust the brightness scale of each of the monochromatic light sources and provide illumination again and re-execute steps S103, S104 and S105.

In more detail, the step S101 is to use the controller 40 to load an image of the standard pattern. The step S102 is to use a plurality of monochromatic light sources of the color-mixing light source device to provide illumination. The step S103 is to use the image capturing device 20 to scan the measurement area 11 to capture the image of the pattern 100 under measurement. The step S104 is to use the controller 40 to convert the image of the pattern 100 under measurement to a gray scale image and use the controller 40 to compare the gray scale image with the image of the standard pattern so as to confirm the matching rate of the gray scale image and the image of the standard pattern. The step S105 is to use the controller 40 to determine that when the matching rate is larger than or equal to a specific value, the controller 40 then further measures width of lines in the gray scale pattern; and if the controller 40 determine that the matching rate is lower than the specific value, the controller 40 then further control the color-mixing light source device 30 to adjust the brightness scale of each of the monochromatic light sources, and provide illumination again and re-execute steps S103, S104 and S105. In an embodiment of the line-width measurement method, the specific value is 80%.

By the above description, comparing with the conventional line-width measurement device that provides only a few choices of colored illumination due to a limited variety of the filter units of a filter, the present invention uses a color-mixing light source device having a plurality of monochromatic light sources that are able to provide 256 kinds of colored illumination by color mixing. Hence, the measurement method of the present invention can provide suitable colored illumination according to the matching rate of the image of the pattern under measurement and the image of a standard pattern, and thereby reducing the difference in color contrast between the gray scale image of the pattern under measurement and the image of the standard pattern to effectively increase the accuracy and stability of line-width measurement.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A line-width measurement device comprising:
a platform having a measurement area;
an image capturing device mounted above the platform and being used to capture an image of a pattern under measurement in the measurement area;
a controller connected to the image capturing device and receiving the image of the pattern under measurement captured by the image capturing device; and
a color-mixing light source device mounted above the platform, including a plurality of monochromatic light sources and adjusting brightness scale of each of the monochromatic light sources according to a matching rate between the image of the pattern under measurement and an image of a standard pattern so as to provide suitable color-mixed lights for illumination, wherein the color-mixing light source device includes a red light source, a blue light source and a green light source, wherein the controller is further used to convert the image of the pattern under measurement to a gray scale image, and then compare the gray scale image with the image of the standard pattern so as to confirm the matching rate between the gray scale image and the image of the standard pattern; the controller is further used to measure the widths of lines in the gray scale image when the matching rate is larger than or equal to 80%, and to control the color-mixing light source device to adjust the brightness scale of each of the monochromatic light sources when the matching rate is lower than 80%.

2. The line-width measurement device as claimed in claim 1, wherein the color-mixing light source device further has an optical element; and the lights emitted by the monochromatic light sources are projected onto the optical element together and mixed with each other, and then are projected outwardly after passing through the optical element.

3. The line-width measurement device as claimed in claim 1, wherein the controller is further connected to the color-mixing light source device and is used to control the color-mixing light source device to adjust the brightness scale of each of the monochromatic light sources according to the matching rate between the image of the pattern under measurement and the image of the standard pattern.

4. The line-width measurement device as claimed in claim 1, wherein the color-mixing light source device has a red light source, blue light source and a green light source which provide 256 kinds of colored illumination by color mixing.

5. The line-width measurement device as claimed in claim 1, wherein the blue light source and the green light source are at least one red light-emitting diode, at least one blue light-emitting diode and at least one green light-emitting diode, respectively.

6. A line-width measurement device comprising:
a platform having a measurement area;
an image capturing device mounted above the platform and used to capture an image of a pattern under measurement in the measurement area;
a color-mixing light source device mounted above the platform, including a plurality of monochromatic light sources and adjusting brightness scale of each of the monochromatic light sources according to a matching rate between the image of the pattern under measurement and the image of a standard pattern, wherein the controller is further used to convert the image of the pattern under measurement to a gray scale image, and then compare the gray scale image with the image of the standard pattern so as to confirm the matching rate between the gray scale image and the image of the standard pattern; the controller is further used to measure widths of lines in the gray scale image when the matching rate is larger than or equal to 80%, and to control the color-mixing light source device to adjust the brightness scale of each of the monochromatic light sources when the matching rate is lower than 80%.

7. The line-width measurement device as claimed in claim 6, wherein the line-width measurement device further comprises a controller, and the controller is connected to the image capturing device and receives the image of the pattern under measurement captured by the image capturing device.

8. The line-width measurement device as claimed in claim 7, wherein the controller is further connected to the color-mixing light source device and is used to control the color-mixing light source device to adjust the brightness scale of each of the monochromatic light sources according to the matching rate between the image of the pattern under measurement and the image of the standard pattern.

9. The line-width measurement device as claimed in claim 6, wherein the color-mixing light source device has a red light source, a blue light source and a green light source which provide 256 kinds of colored illumination by color mixing.

10. The line-width measurement device as claimed in claim 9, wherein the red light source, the blue light source and the green light source are at least one red light-emitting diode, at least one blue light-emitting diode and at least one green light-emitting diode, respectively.

11. The line-width measurement device as claimed in claim 6, wherein the color-mixing light source device further has an optical element; and the lights emitted by the monochromatic light sources are together projected onto the optical element and mixed with each other, and then are projected outwardly after passing through the optical element.

12. A line-width measurement method comprising steps of:
S101: loading a standard pattern;
S102: using a color-mixing light source device having a plurality of monochromatic light sources to provide illumination to a measurement area;
S103: scanning the measurement area to capture an image of a pattern under measurement;
S104: converting the image of the pattern under measurement to a gray scale image and then comparing the gray scale image with the image of the standard pattern so as to confirm a matching rate between the gray scale image and the image of the standard pattern; and
S105: when the matching rate is larger than or equal to 80%, measuring widths of lines in the gray scale image; or when the matching rate is lower than 80%, adjusting the brightness scale of each of the monochromatic light sources and providing illumination again and re-executing steps S103, S104 and S105.

13. The line-width measurement method as claimed in claim 12, wherein the color-mixing light source device has a red light source, a blue light source and a green light source; and adjusting the brightness scale of each of the monochromatic light sources in step S105 is to adjust the brightness scale of the red light source, the blue light source and the green light source.

* * * * *